United States Patent [19]

Pernot

[11] Patent Number: 4,657,427
[45] Date of Patent: Apr. 14, 1987

[54] SYSTEM OF COUPLING OF THE HEAD OF A COUNTER-ANGLE TO THE BODY OF COUNTER-ANGLE

[75] Inventor: Jacques Pernot, Geneuille, France

[73] Assignee: Micro-Mega, Besancon, France

[21] Appl. No.: 707,459

[22] Filed: Mar. 1, 1985

[30] Foreign Application Priority Data

Mar. 8, 1984 [FR] France .................. 84 03732

[51] Int. Cl.$^4$ .............. F16B 21/00; F16B 21/09; F16D 1/00
[52] U.S. Cl. .................. 403/321; 403/322; 403/325; 403/361; 279/1 B; 279/81; 74/527; 74/416
[58] Field of Search .......... 403/321, 322, 325, 327, 403/361, 348; 279/1 B, 77, 79, 81; 74/527, 416

[56] References Cited

U.S. PATENT DOCUMENTS

| | | | |
|---|---|---|---|
| 799,787 | 9/1905 | Gessert | 279/77 |
| 840,734 | 1/1907 | Anderson | 279/77 |
| 1,024,172 | 4/1912 | Bergsten | 279/81 |
| 2,612,377 | 9/1952 | Edens | 279/79 |
| 2,667,357 | 1/1954 | Andreasson | 279/81 |
| 2,854,238 | 9/1958 | Kennell | 279/81 |
| 2,960,343 | 11/1960 | Elledge | 279/81 |
| 3,396,981 | 8/1968 | Hammond | 279/77 X |
| 3,926,532 | 12/1975 | Schlenker et al. | 403/322 |
| 4,055,185 | 8/1977 | Waldron | 279/77 X |
| 4,324,548 | 4/1982 | Nilles et al. | 403/325 X |

Primary Examiner—Cornelius J. Husar
Assistant Examiner—Todd G. Williams
Attorney, Agent, or Firm—Robert E. Burns; Emmanuel J. Lobato; Bruce L. Adams

[57] ABSTRACT

System of coupling of the head of a drive unit to the body of a driven unit, characterized in that, the head bears a longitudinal key having two slopes inclined in relation to the axis of the head, and the body has a guiding or key-way groove for this key, this groove opening on an annular clearing in which a segment can be rotated against a spring and in which a pin is fastened radially, so that, while the key is engaged, this pin, by cooperation with the first of the slopes controls the rotation of the segment, then by cooperation with the second slope controls the blocking of the head in its driving position, and the segment can also be operated by hand so as to free the pin and allow the withdrawal of the head by drawing the key rearwardly.

8 Claims, 8 Drawing Figures

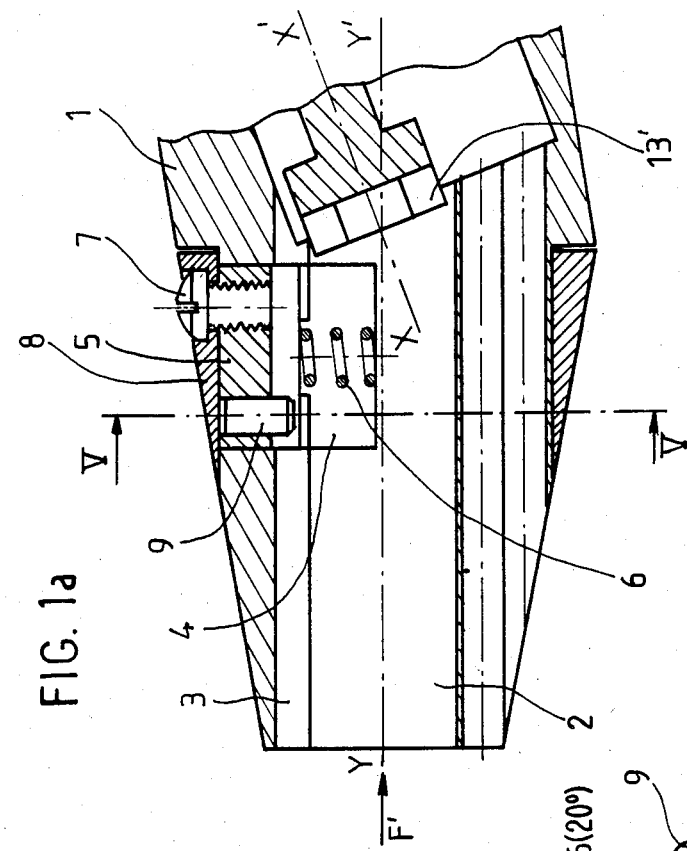
FIG. 1a
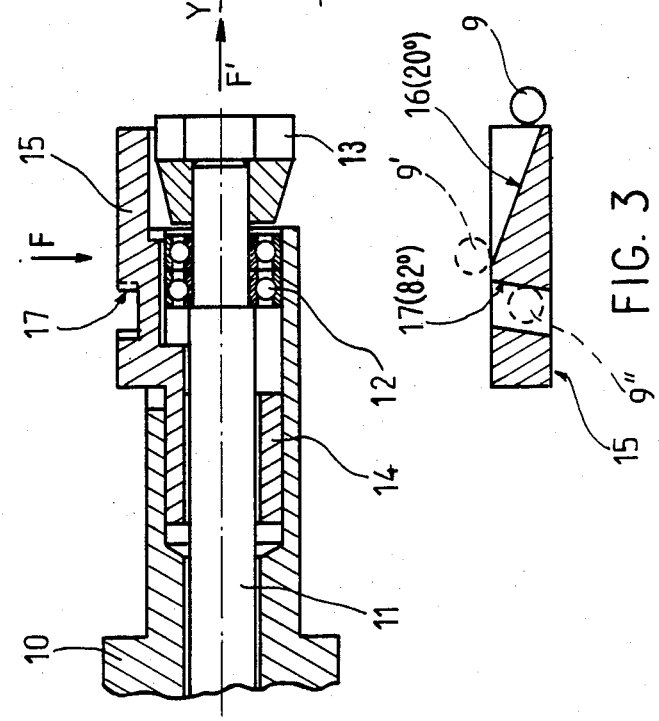
FIG. 1b
FIG. 3

SYSTEM OF COUPLING OF THE HEAD OF A COUNTER-ANGLE TO THE BODY OF COUNTER-ANGLE

FIELD OF THE INVENTION

The present invention concerns a sophisticated system for the automatic coupling of the head of a drive unit to the body of a driven unit.

This system is of the type having a rotating bolt and achieves its simplicity and convenience from means determining automatically by rotation of the barrel of this bolt, instead of requiring from the operator the movement of a ring or other part serving to block the head when it is placed in position for cooperation with the body.

SUMMARY OF THE INVENTION

To this end the system is characterized in that the said head bears an arcuate longitudinal key comprising two slopes inclined in relation to the axis of the head, and the body has a guiding groove or key-way for this key, the groove opening on an annular clearing in which a segment can be rotated against a spring and in which a pin is fastened radially, so that, while the said key is engaged, the pin by cooperation with the first of the slopes controls the rotation of the segment, then by cooperation with the second slope controls the blocking of the head in its engaged position, and the segment can also be operated by hand so as to free the pin and allow the withdrawal of the head by drawing the key rearwardly.

The operation of this system is easy and pleasant since the first slope is not much inclined, and that makes easier the sliding of the pin causing the rotation of the segment playing the role of the barrel of a bolt. This incline can be about 15 to 40°, the slope being long since the angle is small. The locking will be efficient since the second slope will be steep, inclined with an angle of about 75° to 85°, it will be however easy to withdraw the pin, by rotation of the segment with help of an external ring on which it is dependent.

BRIEF DESCRIPTION OF THE DRAWINGS

For now the invention is described more in detail with reference to the attached drawing on which:

FIGS. 1a and 1b illustrate by a sectional axial view the head and the body before coupling one to the other, FIG. 3 is a partially sectional top view showing the profile of the key, as seen along the direction F of FIG. 1b.

On all figures the same components are marked with the same numeral references.

DESCRIPTION OF THE PREFERRED EMBODIMENT

Figure 4:
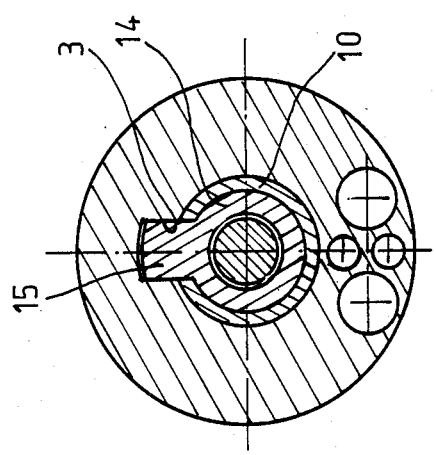
FIG. 4 is a sectional view along line IV—IV of FIG. 1a, FIGS. 5 and 6 are sectional views along lines V—V and VI—VI, respectively, of FIG. 2.
Figure 5:
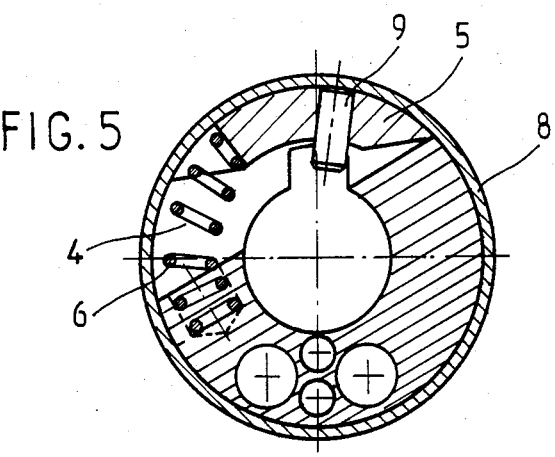
Figure 6:
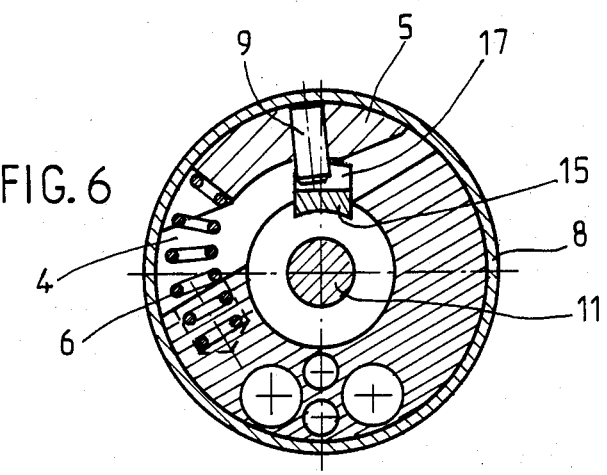
Figure 7:
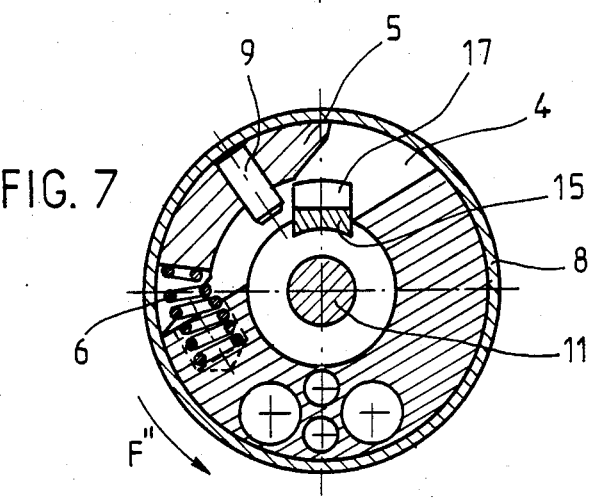
FIG. 7 is a sectional view similar to FIG. 6, but in the position of unlocking of the head.

With reference firstly to FIG. 1a, it is seen that the body 1 of the arena unit of axis YY', having, a groove or key-way 3 (see also FIGS. 2 and 4), and an arcuate cavity in the form of cylindrical sector 4 opening on a portion of the periphery of the body 1. In this cavity 4, following a circular path of axis YY', slides an arcuate segment 5 biased by a compression spring 6. Because of a screw 7, this segment is secured to a ring 8 surrounding the body 1 and in which a pin 9 is fastened, that crosses the segment 5, so that the segment 5, enclosed in the cavity 4 by the ring 8, is secured to the ring for rotation, as FIGS. 5, 6 and 7 illustrate.

Then with reference to FIG. 1b, it is seen that the head 10, of the driving unit containing the shaft 11 borne by the bearing 12 and having gear 13 at its end contains a socket 14 that comprises at its outer end a key 15 having two slopes 16 and 17 (see FIG. 3) are shown in top view in the direction of the arrow F. The slope 16 is inclined forewardly with an angle of 15° to 40° with respect to the axis, and the slope 17 is inclined rearwardly with an angle of 75° to 85°.

Figure 2:
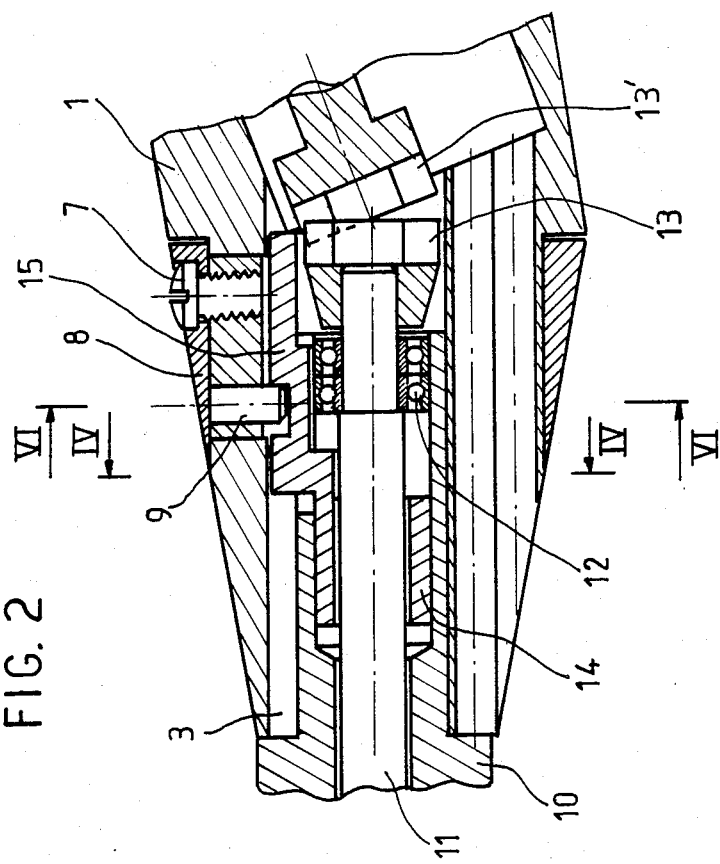
FIG. 2 is a similar sectional view after coupling.

The operation of the device is as follows: while the head 10 is moved into the cylindrical interior opening 2 of the body 1, that is in the direction F', the key 15 slides in the groove or key-way 3, until it contacts the pin 9 (as shown in FIG. 3). At this moment the slope 16 exerts a cam action on the pin 9 that causes the angular displacement of the arcuate segment 5 and of the ring 8, in one angular direction in opposition to the biasing force of the spring 6, until the position 9' is reached (FIG. 3). If the engaging-movement of the head continues until the point where the gear 13 meshes with the gear 13', the pin leaves slope 16 and moves along the other slope 17 (position 9", FIG. 3), under the action of the spring 6, the set segment 5—ring 8 being also drawn back to its initial. The head is then locked onto the body (FIG. 2 and sectional view of FIG. 6).

Conversely, in order to unlock the head, it is enough to turn the ring 8 by hand and compressing the spring 6, that is in the direction F'', so as to free the pin 9 from the key 15 (FIG. 7) and to withdraw the head by pulling it outside the body.

In addition to the ease of handling of this device, two additional advantages can be mentioned:

firstly the head 10 stays firmly in its housing, for the slope 17 increases the action of spring 6. This action is exerted in the axial direction, and it has the effect of correcting for the inevitable progressive wear and consequently of ensuring, firm engagement whatever the wear may be.

secondly as appears clearly in the drawing and notably in FIGS. 2 and 4–7, the device has only a very small bulk, so that there is ample room in body 1, that is available for all the conduits (air, water, light), that are illustrated, at the bottom of each of FIGS. 5–7.

I claim:

1. A system for coupling the head of a driving unit to the body of a driven unit, comprising: a driving unit having a head having a longitudinal key comprising two slopes inclined in relation to the axis of the head, and a driven unit having a body having a cylindrical opening for receiving therein said head of said driving unit and having a key-way for said key, said body having an arcuate cavity into which said key-way opens, spring means seated in said arcuate cavity, a segment seated in said arcuate cavity to undergo circumferential rotation therein and biased by said spring, a pin carried radially by said segment and positioned such that when said head is engaged with said body and the key engages the key-way, the pin by cooperation with the first of said slopes controls the rotation of the segment, then by cooperation with the second slope controls the interlocking of the head and the body, and said segment can also be moved by hand, so as to free the pin and allow the withdrawal of the head from the body by drawing the key rearwardly.

2. A system according to claim 1, wherein the first slope of the key is inclined at an angle of 15° to 40° in relation to the key axis, and the second slope is inclined at an angle of 75° to 85° in the opposite direction.

3. A system according to claim 1, wherein a ring is secured to said segment for freeing the head from the body.

4. A system according to claim 2, wherein a ring is secured to said segment for freeing the head from the body.

5. A system for coupling the head of a driving unit to the body of a driven unit, comprising: a driven unit having an elongated body formed with a cylindrical opening and a key-way both extending axially inwardly from one of its ends, said body having an arcuate cavity extending arcuately in a direction transverse to the axially extending key-way, said key-way opening into said arcuate cavity, a spring seated in said arcuate cavity, an arcuate member seated in said arcuate cavity to undergo angular displacement therein and being biased in one angular direction by said spring, and a radially inwardly extending pin carried by said arcuate member; and a driving unit having a rotationally driven elongated head, said head having an axially extending key at one end for engagement in said key-way when said head is inserted into said cylindrical opening of said driven unit, said key having a first surface and a second surface sloped in relation to the axis of said key for engagement with said pin, said surfaces being sloped in opposite directions, and said key having a recess for receiving said pin, one wall which defines said recess being formed by said second sloped surface to hold said pin in firm engagement when said body and said head are interengaged.

6. A system as defined in claim 5, wherein the first sloped surface is inclined at an angle of 15° to 40° in relation to the key axis, and the second sloped surface is inclined at an angle of 75° to 85° in the opposite direction.

7. A system as defined in claim 5, further comprising a ring seated in said arcuate cavity radially outwardly of said arcuate member and connected to said pin for effecting manual angular displacement of said arcuate member in the other angular direction against the biasing force exerted by said spring.

8. A system as defined in claim 6, further comprising a ring seated in said arcuate cavity radially outwardly of said arcuate member and connected to said pin for effecting manual angular displacement of said arcuate member in the other angular direction against the biasing force exerted by said spring.

* * * * *